(12) United States Patent
Dick et al.

(10) Patent No.: US 6,848,790 B1
(45) Date of Patent: Feb. 1, 2005

(54) METHOD AND DEVICE FOR PERFORMING ONLINE ABERROMETRIE IN REFRACTIVE EYE CORRECTION INDICES

(75) Inventors: Manfred Dick, Gefell (DE); Eckhard Schroeder, Eckental (DE); Joachim Fiedler, Crailsheim (DE)

(73) Assignee: Asclepion-Meditec AG, Jena (DE)

( * ) Notice: Subject to any disclaimer, the term of this patent is extended or adjusted under 35 U.S.C. 154(b) by 0 days.

(21) Appl. No.: 09/807,227

(22) PCT Filed: Aug. 11, 2000

(86) PCT No.: PCT/EP00/07821

§ 371 (c)(1),
(2), (4) Date: Jul. 2, 2001

(87) PCT Pub. No.: WO01/12113

PCT Pub. Date: Feb. 22, 2001

(30) Foreign Application Priority Data

Aug. 11, 1999 (DE) ........................ 199 38 203

(51) Int. Cl.$^7$ ............................... A61B 3/10
(52) U.S. Cl. ................................... 351/205
(58) Field of Search ............................... 351/205, 206, 351/21, 212, 211; 623/6.13, 6.31; 606/5; 356/124

(56) References Cited

U.S. PATENT DOCUMENTS

| | | | | |
|---|---|---|---|---|
| 5,062,702 A | * | 11/1991 | Bille | 351/212 |
| 5,152,788 A | * | 10/1992 | Isaacson et al. | 623/6.13 |
| 5,777,719 A | | 7/1998 | Williams et al. | 351/212 |
| 6,050,687 A | * | 4/2000 | Bille et al. | 351/212 |
| 6,086,204 A | | 7/2000 | Magnante | 351/212 |
| 6,129,722 A | | 10/2000 | Ruiz | 606/5 |
| 6,155,684 A | * | 12/2000 | Bille et al. | 351/212 |
| 6,271,914 B1 | | 8/2001 | Frey et al. | 356/124 |
| 6,299,309 B1 | | 10/2001 | Ruiz | 351/212 |
| 6,379,005 B1 | * | 4/2002 | Williams et al. | 351/211 |
| 6,547,393 B2 | | 4/2003 | Ruiz | 351/212 |
| 6,585,375 B2 | | 7/2003 | Donitzky et al. | 351/219 |

FOREIGN PATENT DOCUMENTS

| | | |
|---|---|---|
| WO | 9201417 | 2/1992 |
| WO | 9927334 | 6/1999 |

OTHER PUBLICATIONS

Klein, A. Stanley, "Optimal corneal ablation for eyes with arbitrary Hartmann–Shack aberrations", *J. Opt. Soc. Am.*, vol. 15, No. 9/Sep. 1998, pp. 2580–2588.

* cited by examiner

*Primary Examiner*—George Manuel
(74) *Attorney, Agent, or Firm*—Davidson, Davidson & Kappel, LLC

(57) ABSTRACT

The invention relates to a method and a device for the complete correction of sight defects in the human eye. Combinations of measuring, and processing methods are described which when applied as disclosed in the invention, make it possible to fully correct sight defects in the human eye. Measuring methods are used which can precisely scan the surface of the cornea and also register other imaging defects in the light path up to the retina. Computer-aided of said measuring results determined when combined with calculation of ideally corrected ocular lenses (for example after cataract operations) or ideally corrected surfaces of the cornea opens up the possibility of manufacturing a patient-specific lens and/or achieving ideal correction of the cornea using preferably a topography-supported spot-scanning-excimer laser system.

31 Claims, 3 Drawing Sheets

METHOD AND DEVICE FOR PERFORMING ONLINE ABERROMETRIE IN REFRACTIVE EYE CORRECTION INDICES

BACKGROUND OF THE INVENTION

The present invention relates to a method and a device for correcting visual defects of the human eye.

In ophthalmology, it is known to shape the cornea by ablation of tissue in the case of amblyopia. In this context, the data on the aberration in the optical path of the eye is obtained by questioning the patient about his/her subjective impression of vision on the basis of corrections via standardized corrective lenses in front of the eye of the patient. Besides, methods exist for measuring the outer contour of the eye with the assistance of stripe- or ring-projection systems as are manufactured, for example, by the Orbtek, Tomey, or Technomed companies.

German Patent Application DE 197 05 119 A1 describes a method for improving a Shack-Hartmann sensor which can be used in the field of astronomy to measure wavefronts for surveying stars.

In German Patent 197 27 573 C1, a device and a method for shaping surfaces, in particular of lenses, by laser ablation of the surfaces is specified in a valuable contribution to the technological development.

It is felt to be a disadvantage of the related art that the correction of the lenses takes place only on the basis of suboptimum data on the causes of the visual defects such as irregularities of the cornea surface or aberration in the optical path. Consequently, only corrections according to the standard lens formulas of geometric optics are carried out.

SUMMARY OF THE INVENTION

Therefore, the object of the present invention is to provide a method and a device which permit complete correction of all refractive visual defects, including the aberrations of the optical path in the defective eye.

In particular, the objective is achieved by a device for correcting visual defects of an eye, including a coherent light source, a beam modification device for shaping and deflecting a beam of the coherent light source, provision being made for a wavefront analyzer device for analyzing a wavefront of the optical path in the eye. This device enables the data obtained from the analysis of the intraocular aberration to be taken into account in the correction of an existing optical system of an eye to be corrected. In this manner, the correction of the optical system of the eye is achievable with added precision.

The considered eye can be, in particular, a human eye but it is also conceivable to correct eyes of other living beings. Visual defects are, in particular, refractive visual defects such as myopia or hyperopia, irregularities of the cornea surface, or aberrations in the optical path.

Provided as coherent light source is preferably a laser, especially preferably a refractive laser, particularly preferably a spot scanning excimer laser. Conceivable is, moreover, a spot scanner using laser light in other ranges of the spectrum, such as a frequency-quintupled YAG laser, an IR laser of around 3 $\mu$m such as an Erbium:YAG laser emitting at 2.94 $\mu$m or a femtosecond laser (fs Laser).

The beam modification device is preferably composed of a device for shaping a beam and of a device for deflecting and aligning the beam. Preferably used as the device for shaping the beam are lens systems, diffractive structures, and refractive elements. Preferably used as the device for deflecting and aligning the beam are scanner arrangements, prisms, and mirrors.

Preferably usable as wavefront analyzer device is a Shack-Hartmann sensor, which is a sensor that is based on a method for analyzing wavefronts and is used, in particular, in astronomy (see above). Using this wavefront analyzer device, it is possible to measure the whole wavefront emerging from the eye and, in this manner, to acquire data on the visual defects, including the intraocular aberration of the optical path also in the eye.

In a further exemplary embodiment of the present invention, provision is made for a device in which a topography analyzer unit for analyzing the surface of the eye is provided, as well. This analysis provides the data on the curvature and contour possessed by the eye surface, i.e., in particular by the cornea. In this manner, the complete data on the refractive visual defects of the eye is available to the system. Both the possibly not optimum surface contour of the eye, i.e., of the cornea, and the intraocular aberration can now be analyzed and are available to the system in the correction of the optical system of the eye. In this manner, it is possible to completely correct the visual defects of the eye and even to achieve a vision which exceeds that of the normal human eye.

In a further exemplary embodiment of the present invention, provision is made for a device in which, moreover, a control unit for processing signals of the wavefront analyzer unit and/or for processing signals of the topography analyzer unit and/or for controlling the coherent light source and/or for controlling the beam modification device is provided. These control units permit evaluation of the data ascertained by the analyzer units. It is possible for the signals of the wavefront analyzer unit and the signals of the topography analyzer unit to be separately processed and evaluated in the control unit, or to process both data sets in one step. The control unit is preferably composed of several individual control units.

This data is preferably used for providing an ideal optical system. The parameters required for beam modification is determined from this data. These parameters can preferably be used in a further step for controlling the coherent light source, for example, to predetermine amplitude, pulse duration, and energy of the beam. Moreover, these parameters are also preferably used for controlling the beam modification device; here, to predetermine the target spot and the geometry of the beam in the target via the deflection of the beam.

Because of this, it is possible in a preferred exemplary embodiment to calculate, in particular, the shot positions for manufacturing the individual elements.

In a further preferred exemplary embodiment of the present invention, provision is made for a device in which the beam modification device is designed in such a manner that an intraocular lens and/or an eye lens and/or the cornea of the eye and/or a contact lens and/or an implantable contact lens (ICL) and/or a spectacle lens are processable via the beam. The beam, which is preferably controlled by the control unit, now enables an element or workpiece of the lens system to be processed in such a manner that the visual defects or aberration are completely corrected. Such an element is preferably an intraocular lens (IOL) which is prefabricated prior to a corresponding operation. This is particularly preferably an ICL (implantable contact lens) which is placed onto the lens. Based on the entire available data on the visual defects, including the aberration of the eye, this IOL or ICL can be shaped in such manner that it corrects all existing visual defects. It is also conceivable for the correction to be carried out on the eye lens itself with the assistance of the beam which is preferably controlled by the, control unit.

Moreover, it is conceivable to carry out a correction by processing the cornea. It is also preferred to manufacture contact lenses which, in a patient-specific manner, correct all individual defects going beyond the refractive eye defect, such as aberrations, unsymmetrical cylinders, and irregularities of the cornea. Besides, it is also possible to manufacture individual spectacle lenses. Besides excimer spot processing, methods of the optical industry, such as the single point diamond turning method, can also be used for this purpose. In this manner, all elements of the affected optical system can be used for correcting the eye defects.

It is also possible to use a combination of the individual (partly) corrected elements. This is an advantage, in particular if the theoretically possible correction via one element would result in excessive stressing of this element, and if such stressing appears not to be advisable, in particular from the medical point of view.

In a further preferred exemplary embodiment of the device according to the present invention, the control unit is designed in such a manner that the analysis of the optical path in the eye and/or the analysis of the surface of the eye can be carried out virtually simultaneously with the processing of an optical element via the beam of the coherent light source. Due to this modification of the control unit, an "online" test of the optical path in the eye such as it is currently modified via the operation and/or of the surface of this eye at the current point of time can be carried out during the processing of the optical element, i.e., for example during the processing of the cornea via the surgical laser beam, and be taken into account in the further operation or processing. During a laser treatment of the cornea for correcting refractive visual defects of the eye, it is thus possible for the prevailing refractive value of the overall visual apparatus of the eye to be continuously measured and for the sequence of treatment to be exactly adjusted online to the target value of the refraction of the eye in the case that disturbing influences on the treatment are present. This optimized treatment is made possible by this combination of the optical systems of a surgical laser for the ablation of cornea tissue or lens material and of an aberrometer for the analysis of wavefronts or of the surface of the eye. Particularly advantageous in this context is the complete ascertainment of the refractive values (spherocylindrical aberrations and aberrations of higher order) of the whole optical apparatus of the eye which, in the final analysis, are representative of the quality of the attained surgical intervention. By performing the ascertainment completely online and without interrupting the sequence of treatment, provision is made for an optimized device in terms of the time sequence and the attainable precision.

Particularly preferably, it is also possible for the analysis of the optical path or of the surface of the eye to be carried out in alternation with the processing of the optical element, thus ascertaining portion-by-portion the progression of the treatment or of the operation of the optical system, in particular of the cornea. It is also conceivable for the scanning and analysis of the optical path or of the surface of the eye to be time-interleaved with the processing via the surgical laser beam. This permits continuous or virtually continuous measurement combined with real device integration (e.g., every second) and continuous recalculation of the laser control.

Moreover, the objective is achieved by a method according to the present invention for correcting visual defects of an eye, the optical path of the eye being determined via a wavefront analysis, and an ideal lens system being calculated which would result in a correction of the visual defects of the eye. This method is particularly preferably employed using a device according to the present invention. In this method, the intraocular aberration of the optical path is available for calculating the correction of the optical system for conversion into an ideal optical system.

In a further method according to the present invention, it is particularly preferred to analyze the topography of the eye as well. In this method, consequently, additional data on the defective vision of the eye is available, in particular on aberrations, unsymmetrical cylinders, and irregularities of the cornea.

In another preferred method, the ideal optical system is provided on the basis of the data obtained from the wavefront analysis and/or from the topography analysis. For this, it is particular preferred to provide only one element from this optical system. In this manner, the correcting element or the correcting elements is/are manufactured in a further step on the basis of the complete data of the defective vision. This procedure thus leads to the complete correction of the defective vision.

In a further preferred method, shot positions for manufacturing the ideal optical system are calculated using the data obtained from the wavefront analysis and/or from the topography analysis. In this manner, it is advantageously possible to use the laser spot excimer method for manufacturing the individual elements of the optical systems. The shot positions are optimized depending on the materials to be used and considering the time needed for manufacture.

In another method of the present invention, the old optical system of the eye is reshaped into the calculated ideal optical system. To this end, either elements of the old optical system are processed directly or correspondingly corrected elements are manufactured and inserted or old elements are replaced with new elements. This method allows the old (defective) optical system of the eye to be converted into a (new) ideal optical system. It is especially preferred to manufacture a new lens or an ICL according to the spot scanning principle using an excimer laser.

It is particularly preferred in the method according to the present invention to process a contact lens which is already located on the eye of the patient. During measurement, the patient preferably wears already a contact lens correcting standard visual defects or, in the case of emmetropia, only a therapeutic contact lens which especially preferably features good adhesion and constant image characteristics without decentering. Now, the ablation is carried out on the standardized contact lens, thus non-invasively attaining a riskless correction of the higher aberration of the eye. This allows, in particular, higher aberrations to be corrected without risk to the patient and with high treatment safety to enable the optical apparatus of the eye to utilize the resolving power of the retina and to be provided with a supervision which is superior to that of the normally-seeing eye. Regardless of the characteristics of their own eyes in terms of transmittance values or drying of the tear film, patients can now acquire a preferred super-vision and gain experience therewith in everyday life. The old vision characteristic is restored by removing the contact lens.

For this purpose, it is also preferred to use a therapeutic contact lens without refractive effect. In this connection, all image defects are corrected on this contact lens with the assistance of the laser.

It is particularly preferred to use contact lenses made of PMMA or plastic lenses which, compared to the human cornea, especially preferably feature a small material ablation for the used laser, for example, a 193 nm ArF excimer laser. Particularly preferred are also all soft contact lenses which exhibit nearly the same ablation characteristics as the cornea because of their high water content. Thus, it is possible to determine the exact ablation rates for any standardized-manufacture contact lens material prior to the treatment and, because of this, to carry out a desired refractive correction on the eye in a reproducible manner.

The correction possibility simulated in this manner can serve in a preparatory manner for a later real cornea operation, or such a lens having a customized correction can be used for a predetermined time. In particular in the case of hard contact lenses, longer-term use is also possible. In this context, a corresponding marking for the axial orientation is applied which is paid attention to during insertion.

The optical system preferably includes, as elements, the eye lens and/or an intraocular lens and/or the cornea of the eye and/or a contact lens and/or an ICL and/or at least one spectacle lens. Via refractive surgery, it is possible, for example, for the cornea of the eye to be reshaped so as to correct the existing defective vision (for example, the surface of the cornea via photorefractive keratectomy, PRK, or by ablation of inner tissue layers of the cornea using laser assisted in situ keratomileusis, LASIK). These elements not only feature rotationally geometric corrections but individual structures for correcting the defective vision of the patients. In this manner, it is possible to manufacture intraocular lenses or contact lenses, in particular ICLs which, once they are brought into the lens system, not only roughly correct the defective vision of the eye as in known methods heretofore but which additionally correct all irregularities, unsymmetries, and beam distortions, as well. In this manner, it is possible to attain a vision which exceeds that of the normal human eye. Besides, this method makes it possible to manufacture spectacle lenses which likewise correct all irregularities, unsymmetries, and beam distortions of the defective eye or of the old optical system, as well.

Moreover, the objective is achieved by an ideal optical system which is manufactured according to a method according to the present invention and/or using a device according to the present invention, the optical system including elements made of materials which are suitable for implantation and/or for adhesion and/or for ablation, in particular plastic or glass. By selecting these materials of the lens system according to the present invention, compatibility in using these elements is guaranteed. Such materials are, for example, PMMA, acrylic, silicone, or a combination of these materials.

In a further exemplary embodiment of the present invention, provision is made for an ideal optical system including elements which contain refractive and/or diffractive structures. In known methods heretofore, refractive and/or diffractive structures are only used in beam shaping. A minilens system guides and shapes the entering beam to attain a special beam distribution in the target plane. The use of such refractive and/or diffractive structures on individual elements of an optical system allows visual defects to be selectively corrected in an exceptionally ideal manner. Using these structures, it is thus possible to correct individual, non-steady aberrations but also to give the optical systems characteristics which a normal human eye does not possess.

The objective of the present invention is achieved, moreover, by an element of an (ideal) lens system having refractive and/or diffractive structures. Such elements can include intraocular lenses, modified cornea, contact lenses, ICLs, or spectacle lenses.

BRIEF DESCRIPTION OF THE DRAWINGS

In the following, exemplary embodiments of the present invention and advantageous refinements will be explained in greater detail on the basis of drawings. In this context.

DETAILED DESCRIPTION

Figure 1:
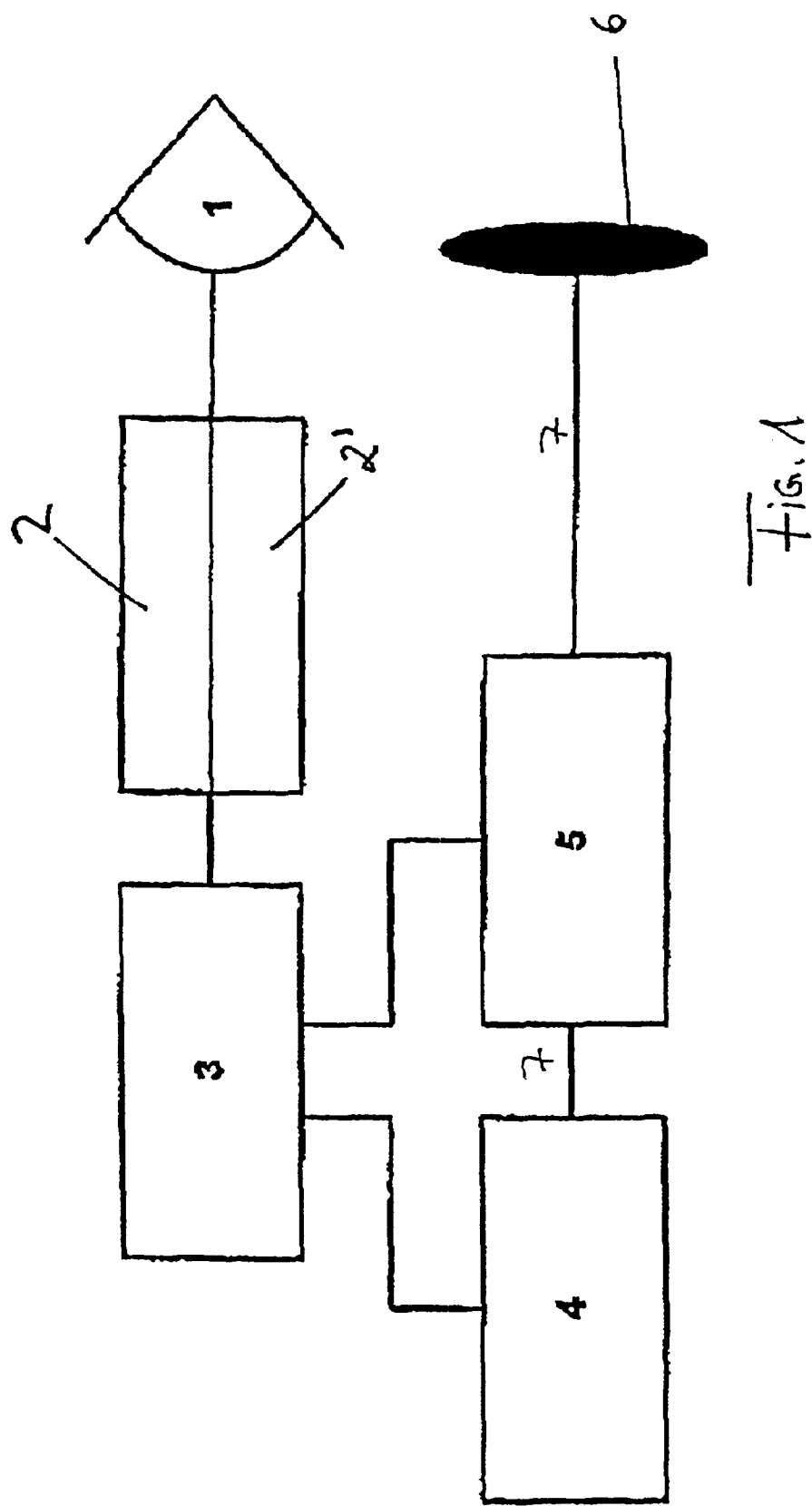
FIG. 1 shows a block diagram for an exemplary embodiment of a device according to the present invention for correcting an aberration in the optical path of an eye on a lens 6.

FIG. 1 depicts a block diagram for an exemplary embodiment of a device according to the present invention for correcting visual defects of an eye on a lens. A wavefront analyzer unit 2 and a topography analyzer unit 2' are connected to a control unit 3. Control unit 3 is connected to a laser 4 and to a beam modification device 5 via a bus. A lens 6 is depicted downstream of beam modification device 5. An eye 1 is shown upstream of wavefront analyzer unit 2 and topography analyzer unit 2'.

In the operating state, the beams of wavefront analyzer unit 2 and topography analyzer unit 2' scan eye 1 and transmit the obtained signals to control unit 3. The beams which are used here are preferably beams of a coherent light source, especially preferably beams of an IR diode or of a green laser. In control unit 3, the signals are processed and the ideal optical system for this eye 1 is calculated. In the depicted case, an ideal lens 6 is calculated here as element of the optical system. In control unit 3, in particular, all shot positions needed for laser 4 to manufacture ideal lens 6 are calculated on the basis of the data obtained from the signals, taking into account the laser-relevant data. Subsequently, control unit 3 triggers laser 4, determining energy and pulse rate of beam 7. Beam 7 is guided through beam modification device 5. In beam modification device 5, beam 7 is shaped and deflected via scanners and lens systems according to the calculated shot positions via the input of control unit 3, so that customer-specific lens 6 is manufactured by ablation of material on the raw lens via controlled surgical laser beam 7. Preferably, control unit 3 can also be designed in several partial control units which can be connected to individual components of the device.

Figure 2:
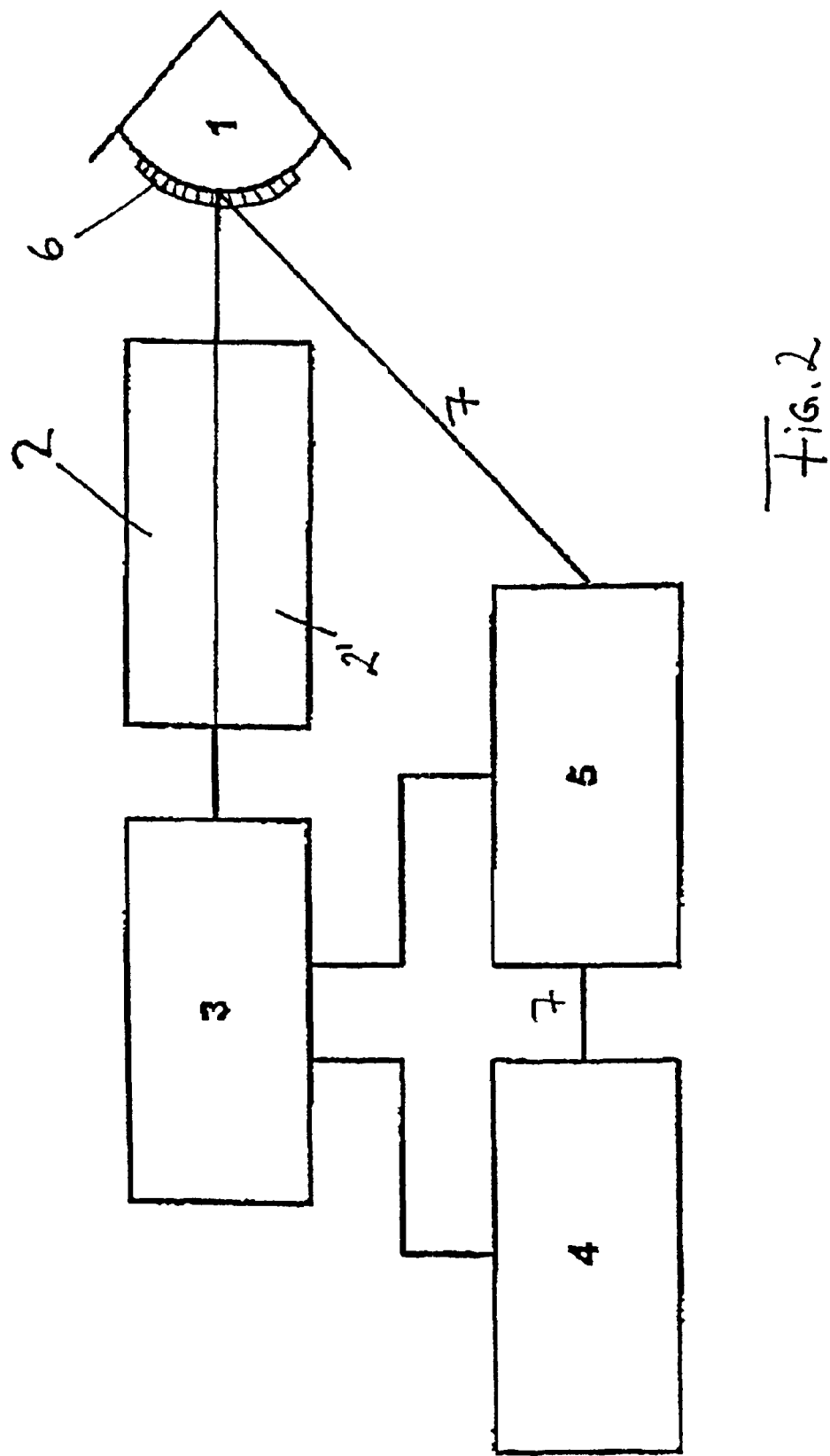
FIG. 2 shows a block diagram for an exemplary embodiment of a device according to the present invention for correcting an aberration in the optical path of an eye to which a lens 6 is applied.

FIG. 2 depicts a block diagram for a further exemplary embodiment of a device according to the present invention for correcting an aberration in the optical path of an eye to which a lens is applied. In principle, the configuration corresponds to that of FIG. 1 with the difference that a contact lens 6 is directly applied to eye 1 and that the ablation is carried out there in situ. To this end, surgical leaser beam 7 is directed, preferably via further optical elements such as mirrors (not shown), to lens 6 which rests directly on eye 1. The ablation of the lens material is now carried out in situ on the eye so that the optical path in the system of eye 1 and lens 6 as well as the surface of this system, i.e., here preferably of lens 6, can now be analyzed, preferably online, via analyzer device 2 or 2' concurrently with the ablation, and the treatment via beam 7 can be directly checked and assessed. Ideal lens 6 manufactured in this manner now conveys to the interested it person an impression of the complete optical system and of the surgical conditions without having undergone an irreversible operation.

Figure 3:
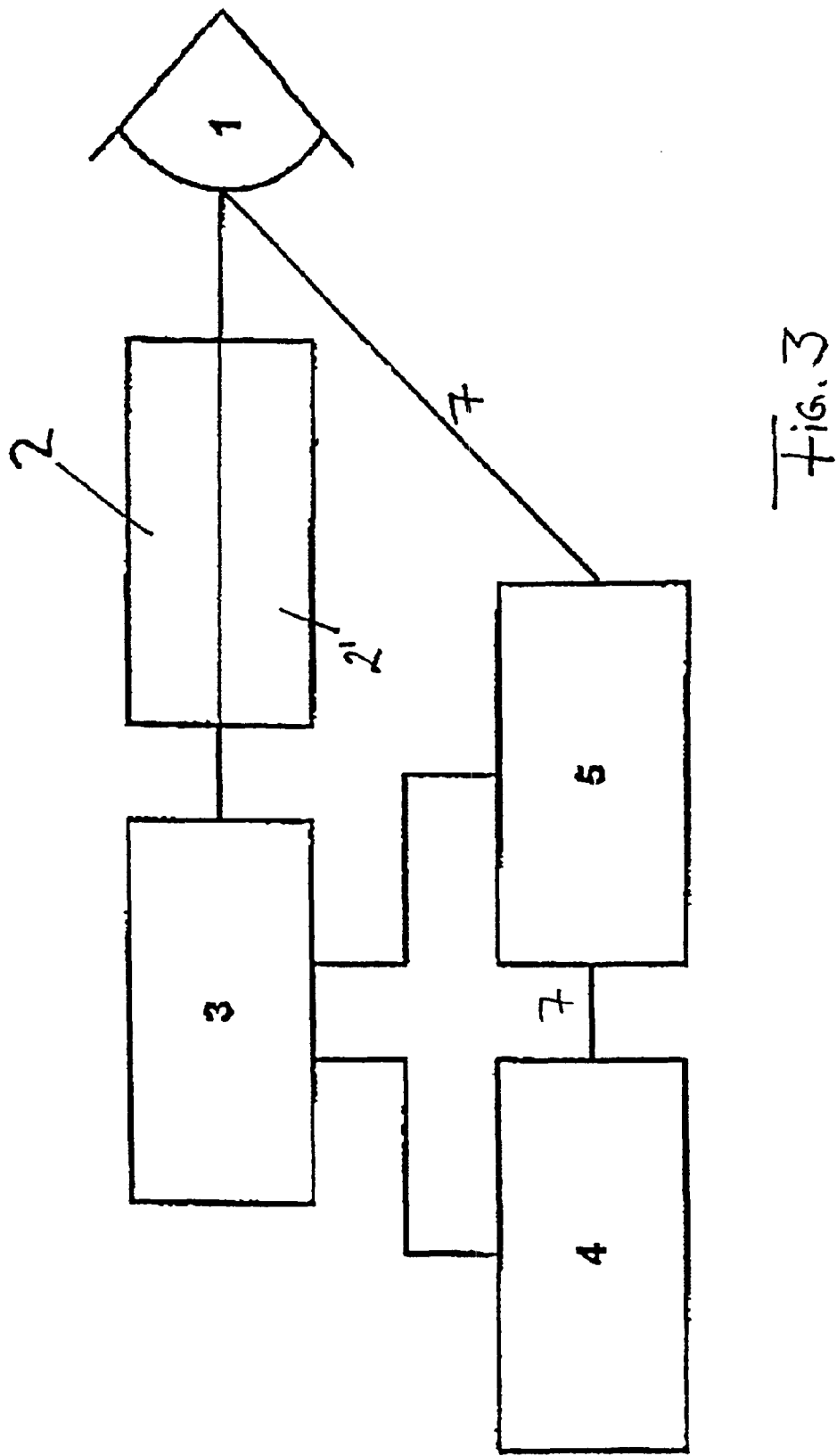
FIG. 3 shows a block diagram for an exemplary embodiment of a device according to the present invention for correcting an aberration in the optical path of an eye on without contact lens.

FIG. 3 depicts a block diagram for an exemplary embodiment of a further device according to the present invention for correcting the aberration in the optical path of an eye without contact lens. Here, preferably simultaneously with the analysis of eye 1 via analyzer device 2, 2', the progression of the operation can be monitored online via the surgical beam 7, and recalculations can be carried out via control unit 3 during the operation so that eye 1 can be treated iteratively via laser beam 7 which reacts and is used in each case as a function of the prevailing conditions. Besides, the progression of the operation can also be monitored visually, for example, via a microscope (not shown).

It is particularly preferred to project a point onto the retina of eye 1 with the assistance of a light source of analyzer device 2, 2' (light source not separately shown). In this context, a nearly parallel external optical path is used, making use of the focusing effect of the optical apparatus of the eye to be able to generate an as small as possible point. In accordance with the used wavelength and the irradiation time, the intensities are so small that no damage can occur on the retina but sufficient reflected intensity exists.

While passing through the aberrative optical system of the eye, the reflective wave detects all image defects. The correspondingly deformed wavefront reaches wavefront analyzer device 2 or topography analyzer device 2' from where the aberration data is preferably fed to a computer via a corresponding electronics or control unit 3. With the assistance of the computer software, a current ablation profile is in each case calculated from the aberration data, the ablation profile triggering excimer laser 4 including the spot scanning system, implementing a target-controlled treatment via beam modification device 5.

Such a measurement can also be carried out sporadically, for example, during 80 percent of the treatment time. Analyzer device 2 or 2' can be arranged on a separate stand so that laser and measuring instrument swing in alternately or, preferably, the measuring instrument is integrated in the laser and measures when the laser bombardment is interrupted. It is particularly preferred for a recalculation of the remaining treatment to be carried out on request of the operator. This measurement can particularly preferably be carried out also continuously or virtually continuously in the case of device integration and continuous recalculation of the laser control.

In this manner, a new and advantageous method and a device for completely correcting visual defects of the human eye have been specified. Combinations of measuring and processing methods have been specified which, when used according to the present invention, enable the human eye to be completely corrected. In doing so, measuring methods are used which can precisely measure the surface of the cornea and which also record the aberrations arising in the further optical path up to the retina. The computer-aided evaluation of these measuring results, in conjunction with the calculation of ideally corrected eye lenses (for example, after cataract operations) or of ideally correcting cornea surfaces, makes it possible to manufacture a patient-specific lens and/or to shape the cornea in an ideally correcting manner, preferably using a spot scanning excimer laser system in a topography-aided manner.

In particular, the correction can be effected via the modification of an element of the optical system. Thus, for improving the vision of a patient having a cataract and a defective vision, it is sufficient to completely correct the intraocular lens. In such a case, it is no longer necessary to carry out a refractive operation in addition to the cataract operation.

LIST OF REFERENCE SYMBOLS

1 Eye
2 Wavefront analyzer device
2' Topography analyzer unit
3 Control unit
4 Coherent light source
5 Beam modification device
6 Optical element/lens

What is claimed is:

1. A device for correcting visual defects of an eye comprising:
    a coherent light source,
    a wavefront analyzer device for analyzing a wavefront of an optical path in the eye,
    a topography analyzer unit for analyzing the surface of the eye,
    a control unit configured to process signals of the topography analyzer unit and the wavefront analyzer device and to calculate a plurality of shot positions using the signals, and
    a beam modification device configured to shape and deflect a beam of the coherent light source according to the plurality of calculated shot positions for processing an optical element.

2. The device as recited in claim 1, wherein the control unit is configured for controlling at least one of the coherent light source and the beam modification device.

3. The device as recited in claim 2, wherein the control unit is designed in such a manner that the processing of the signals can be carried out virtually simultaneously with a processing of the optical element via the beam of the coherent light source.

4. The device as recited in claim 1, wherein the optical element includes at least one of an intraocular lens; an eye lens; the cornea of the eye; a contact lens; an implantable contact lens (ICL); and a spectacle lens.

5. The device as recited in claim 1, wherein the coherent light source is a laser.

6. The device as recited in claim 5 wherein the laser is a spot scanning excimer laser.

7. An ideal optical system manufactured using one of the devices according to claim 1 wherein the optical system includes elements made of materials which are suitable for at least one of implantation; adhesion; and ablation.

8. The system as recited in claim 7 wherein the materials are plastic or glass.

9. A method for correcting visual defects of an eye comprising:
    determining an optical path of the eye via a wavefront analysis;
    analyzing a topography of the eye;
    calculating a plurality of shot positions using a control unit using data obtained from the wavefront analysis; and
    shaping and deflecting a beam according to the plurality of calculated shot positions using a beam modification device so as to process an ideal optical system which would result in a correction of the visual defects of the eye.

10. The method as recited in claim 9, wherein the ideal optical system is provided as a function of data obtained from the wavefront analysis and wherein the shaping and deflecting is performed virtually simultaneously with at least one of the determining and the analyzing.

11. The method as recited in claim 9, wherein the calculating of the plurality of shot positions is performed as a function of data obtained from the wavefront analysis and the topography analysis.

12. The method as recited in claim 9 further comprising reshaping the old optical system of the eye into the calculated ideal optical system.

13. The method as recited in claim 9, wherein the optical system includes at least one of the eye lens; an intraocular lens; the cornea of the eye; a contact lens; an ICL; and at least one spectacle lens.

14. An ideal optical system manufactured according to the method of claim 9 wherein the optical system includes elements made of materials which are suitable for at least one of implantation; adhesion; and ablation.

15. The ideal optical system as recited in claim 14 wherein the optical system includes elements having refractive and/or diffractive structures.

16. The system as recited in claim 14 wherein the materials are plastic or glass.

17. A device for correcting visual defects of an eye comprising:
a light source,
a topography analyzer unit for analyzing the surface of the eye;
a wavefront analyzer device for analyzing a wavefront of an optical path in the eye;
a control unit configured to process signals of the wavefront analyzer device and to calculate a plurality of shot positions using the signals;
a beam modification device configured to shape and deflect a beam of the light source according to the plurality of calculated shot positions for processing at least one of an intraocular lens and an implantable contact lens.

18. The device as recited in claim 17, wherein the control unit is configured for processing first signals of the wavefront analyzer unit and processing second signals of the topography analyzer unit and wherein the calculating is performed using the first and second signals.

19. The device as recited in claim 18, wherein the control unit is configured such that a processing of the the intraocular lens or implantable contact lens via the beam of the light source can be carried out virtually simultaneously with at least one of an analysis of the optical path in the eye and an analysis of the surface of the eye.

20. A method for correcting visual defects of an eye comprising:
determining an optical path of the eye via a wavefront analysis;
analyzing a topography of the eye;
calculating a plurality of shot positions for a beam of a light source needed to achieve an ideal optical system which would result in a correction of the visual defects of the eye, the calculating being performed using data from the wavefront analysis; and
processing at least one of an intraocular lens and an implantable contact lens by deflecting the beam according to the plurality of calculated shot positions using a beam modification device so as to correct the visual defect.

21. The method as recited in claim 20, wherein the processing is performed virtually simultaneously with at least one of the determining of the optical path of the eye and the analyzing of the topography of the eye.

22. A device for correcting visual defects of an eye comprising:
a coherent light source,
a beam modification device configured to shape and deflect a beam of the coherent light source according to the plurality of shot positions for processing an optical element; and
a wavefront analyzer device emitting signals corresponding to a wavefront of an optical path in the eye, and
a control unit processing the signals from the wavefront analyzer device so as to analyze the wavefront and to calculate the plurality of shot positions based on the wavefront analysis and the control unit simultaneously controlling at least one of the beam modification device and the coherent light source so as to process the optical element.

23. The device as recited in claim 22, further comprising a topography analyzer unit for processing second signals corresponding to the surface of the eye, and wherein the control unit processes the second signals.

24. The device as recited in claim 22, wherein the optical element includes at least one of an intraocular lens; an eye lens; the cornea of the eye; a contact lens; an implantable contact lens (ICL); and a spectacle lens.

25. The device as recited in claim 22, wherein the coherent light source is a laser.

26. A method for correcting visual defects of an eye comprising:
determining an optical path of the eye via a wavefront analysis;
calculating an ideal optical system which would result in a correction of the visual defects of the eye;
calculating, using the wavefront analysis, a plurality of shot positions needed for processing an optical element so as to achieve the ideal optical system; and
simultaneously processing the optical element using a beam modification device.

27. The method as recited in claim 26, further comprising analyzing a topography of the eye simultaneously with the processing.

28. The method as recited in claim 27, wherein the calculating of the plurality of shot positions is performed as a function of data obtained from the wavefront analysis and the topography analysis.

29. The method as recited in claim 26, wherein the ideal optical system is provided as a function of data obtained from at least one of the wavefront analysis and the topography analysis.

30. The method as recited in claim 26 further comprising reshaping the old optical system of the eye into the calculated ideal optical system.

31. The method as recited in claim 26, wherein the optical system includes at least one of the eye lens; an intraocular lens; the cornea of the eye; a contact lens; an ICL; and at least one spectacle lens.

* * * * *